United States Patent [19]

Beschke et al.

[11] 4,314,064
[45] Feb. 2, 1982

[54] PROCESS FOR THE PRODUCTION OF NICOTINAMIDE

[75] Inventors: Helmut Beschke; Heinz Friedrich, both of Hanau; Klaus-Peter Müller, Bergheim; Gerd Schreyer, Hanau, all of Fed. Rep. of Germany

[73] Assignee: Detusche Gold- und Silber-Scheindeanstalt vormals Roessler, Frankfurt, Fed. Rep. of Germany

[21] Appl. No.: 192,038

[22] Filed: Sep. 29, 1980

Related U.S. Application Data

[63] Continuation of Ser. No. 676,198, Apr. 12, 1976, abandoned.

[30] Foreign Application Priority Data

Apr. 17, 1975 [DE] Fed. Rep. of Germany ....... 2517054

[51] Int. Cl.$^3$ ............................................ C07D 213/56
[52] U.S. Cl. .................................. 546/317; 546/319
[58] Field of Search ....................... 546/316, 317, 323

[56] References Cited

U.S. PATENT DOCUMENTS 2,446,957  8/1948  Rosenberg ........................ 546/316
2,471,518  5/1949  Duesel et al. ..................... 546/316

*Primary Examiner*—Alan L. Rotman
*Attorney, Agent, or Firm*—Cushman, Darby & Cushman

[57] ABSTRACT

Nicotinamide is prepared from nicotinonitrile by hydrolysis at 120° to 200° C. employing alkali hydroxide.

12 Claims, No Drawings

PROCESS FOR THE PRODUCTION OF NICOTINAMIDE

This is a continuation of application Ser. No. 676,198, filed Apr. 12, 1976, now abandoned.

The invention is directed to a process for the production of nicotinamide from nicotinonitrile by hydrolysis at elevated temperature using alkali hydroxide.

Several processes are known for the production of nicotinamide by the hydrolysis of nicotinonitrile using alkaline acting materials. Thus, there can be used alkaline earth metal oxides or carbonates (British Pat. No. 777,517) alkaline ion exchangers (J.Am.Chem.Soc. Vol. 70 (1948), 3945), manganese dioxide (German Ausleges-chrift No. 2,131,813), sodium hydroxide in admixture with hydrogen peroxide (German Pat. No. 828,247), as well as sodium hydroxide, ammonia or alkaline acting salts (U.S. Pat. No. 2,471,518). In these processes one is either content with a partial reaction of the nitrile and attaining a high selectivity, i.e., there is substantially avoided the formation of byproducts, especially nicotinic acid, or one obtains a substantial reaction of the nitrile and there is produced a substantial amount of byproducts. The yield of nicotinamide at best is 86%.

In the process above in which sodium hydroxide is used, the hydrolysis is carried out at temperatures up to 100° C. To be sure the nitrile is substantially reacted, however, the yield of amide is below 60%. To recover the amide the reaction mixture is evaporated to dryness. The amide remaining as residue is so impure that it must be purified by extraction or recrystallization before it can be used further.

There has now been found a process for the production of nicotinamide from nicotinonitrile by hydrolysis at elevated temperature using alkali hydroxide in which the hydrolysis is carried out at temperatures between about 110° to 250° C. The nitrile is nearly completely reacted by this process. Surprisingly, the hydrolysis thereby results almost exclusively in the formation of nicotinamide. Nicotinic acid is formed only in an amount equivalent to the alkali used. The amide accumulates in such a high purity that it generally can be further used directly, for example as a fodder additive.

The hydrolysis according to the invention is carried out at temperatures of about 110° to 250° C., preferably about 120° to 200° C., especially 135° to 200° C. The pressure essentially depends upon the temperature and generally is 1.5 to 40 bar, especially 3 to 20 bar.

The hydrolysis takes place in aqueous medium in the presence of alkali hydroxide, preferably sodium hydroxide or potassium hydroxide. Suitably there is added in general about 0.3 to 3.0 moles, especially 0.5 to 2.5 moles of alkali hydroxide per 100 moles of nicotinonitrile. Suitably there is used an aqueous alkali hydroxide solution whose concentration of alkali hydroxide does not substantially exceed 20 weight % and generally is between about 1 and 10 weight %. It can be advantageous to add the alkali hydroxide gradually in portions in the course of hydrolysis.

A continuous operation is particularly advantageous, using for this purpose customary apparatus such as cascades of reaction vessels, loop reactors or flow tubes. Preferably the reaction is carried out, at least at the end, in a flow tube.

The nicotinonitrile is suitably fed in as an aqueous solution at a concentration of 5 to 70 weight %, especially 20 to 60 weight %, which solution is preferably preheated to at least 70° C. The alkali hydroxide likewise is suitably added as an aqueous solution, namely preferably in several parts in the course of the hydrolysis. The addition of the alkali hydroxide is so regulated that at the end there is present a hydrolysis mixture which has a pH below 9.5, especially below 8.5. The hydrolysis mixture can have a final pH as low as 7.0.

The throughput is suitably so regulated that the hydrolysis mixture has an average residence time of 1 to 20 minutes, especially 3 to 15 minutes and results in a yield of 1 to 20 kg, especially 2 to 10 kg of nicotinamide per hour and per liter of reactor volume.

The nicotinamide can be recovered in known manner from the resultant hydrolysis mixture, especially by evaporating the mixture to dryness at temperatures of up to about 100° C., if necessary using reduced pressure.

However, it has proven advantageous to drive off the water from the hydrolysis mixture at temperatures about 130° C., preferably at temperatures of about 140° to 200° C., especially 150° to 180° C., in a given case at reduced pressure. In using these temperatures the nicotinamide remains as a melt which solidifies as crystals in the cooling.

In the continuous carrying out of the hydrolysis, this type of dehydrating or drying the hydrolysis mixture is especially favorable, namely, the dehydration is carried out with advantage directly after the hydrolysis and likewise is carried out continuously. Falling film evaporators are especially suitable apparatus for this purpose. Preferably two evaporators are connected in succession. Suitably the first of these is operated at normal pressure and the second so operated at pressures below 0.2 bar that the first provides a melt having about 1 to 5 weight percent water and the second provides a melt having less than 0.5 weight percent water. The melt is solidified, suitably with slow cooling, brought to crystallization, advantageously using a cooling belt.

Nicotinamide recovered in this manner is directly suitable as a fodder additive. In the event that the nicotinamide should be recovered free of nicotinic acid, for example for pharmaceutical purposes, the melt is introduced with stirring into a liquid which is a selective solvent for the nicotinamide. There are suitable as liquids, for example ketones, alcohols and esters, especially acetone, methyl ethyl ketone, propanol-2, butanol-2, and 2-methylpropanol-1.

Unless otherwise indicated all parts and percentages are by weight.

EXAMPLE 1

There was used a 9 meter long flow tube filled with packing of wire screens and a free diameter of 25 mm. There was an inlet pipe for the nicotinonitrile solution at the beginning of the tube and three inlet pipes for the alkali hydroxide solution, one being at the beginning of the tube, the second after 3 meters and the third after 6 meters of the length of the tube. There was fed in a uniform stream hourly a solution of 10.0 kg of nicotinonitrile in 13.5 kg of water heated to 130° C. Besides there was added a 10% aqueous sodium hydroxide solution, namely from this solution there was led in hourly in uniform flow 113 grams at the beginning of the tube, 225 grams after 3 meters and 415 grams after 6 meters of tube length. The tube was held at 130° C. over the entire length by heating or cooling. The pressure in the tube was 4 bar.

The hydrolysis mixture which was drawn off from the tube at the end had a pH value of 8.0. It was led directly into a falling film evaporator having a diameter of 40 mm and a length of 3 meters, which was heated with steam at a pressure of 9 bar to 170° C. The melt of nicotinamide which was delivered from this evaporator contained 2.4 weight % of water. It was led to a second falling film evaporator which was heated to 170° C. and operated at a pressure of 0.03 bar. The melt which was recovered from this evaporator had a water content of 0.2 weight %. There was accumulated in the falling film evaporators as distillate an aqueous solution which hourly contained 0.4 kg of nicotinonitrile. From the second falling film evaporator the melt was directly led to a steel cooling belt having a length of 4 meters and a width of 0.3 meters. The cooling belt, that had a speed of 0.15 meters per second was not cooled in the first third and was water cooled in the following two thirds.

The product cooled on the belt was comminuted with a breaker and ground with a spike mill. The yield was 11.3 kg per hour. The product consisted of 97.2 weight % nicotinamide and also contained 2.4 weight % sodium nicotinate, 0.05 weight % nicotinonitrile and 0.25 weight % water. The product was suitable directly for use as a fodder additive.

EXAMPLE 2

The process was the same as in Example 1 except the temperature in the flow tube was 160° C. and the pressure 8 bar. The nicotinonitrile solution was fed in with a temperature of 160° C. There was introduced 10 weight % of sodium hydroxide solution, there being employed per hour 113 grams at the beginning of the tube, 113 grams after 3 meters and 225 grams after 6 meters of the tube length. The yield per hour was 10.9 kg. The composition of the product was 98.2 weight % nicotinamide, 1.5 weight % sodium nicotinate, 0.05 weight % nicotinonitrile and 0.2 weight % water.

EXAMPLE 3

The process was the same as in Example 1 but the melt was not led out of the second falling film evaporator to a cooling belt but was introduced with stirring into 2-methylpropanol-1. There were added hourly 21.7 kg of 2-methylpropanol-1 which was held at the boiling point. The mixture was filtered hot. There remained 500 grams of filter residue per hour, which residue was essentially sodium nicotinate. There was separated from the filtrate by cooling to 5° C. the nicotinamide, namely 9.6 kg per hour was recovered. The nicotinamide was sufficiently pure for pharmaceutical purposes. In evaporation of the mother liquor there was accumulated 1.1 kg of nicotinamide contaminated with sodium nicotinate. By recrystallization there was recovered from this 0.8 kg of pure nicotinamide.

The process can comprise, consist essentially of or consist of the steps set forth with the materials recited.

What is claimed is:

1. A continuous process for the production of nicotinamide from nicotinonitrile comprising hydrolyzing the nicotinonitrile using about 0.3 to 3.0 moles of an alkali metal hydroxide per 100 moles of nicotinonitrile at about 120° to 200° C. at pressures of 3 to 20 bar.

2. The process of claim 1 wherein the hydrolysis is carried out at a temperature of about 135° to 200° C.

3. The process of claim 2 wherein there is used in the hydrolysis about 0.3 to 3.0 moles of alkali hydroxide per 100 mole of nicotinonitrile and the alkali hydroxide is sodium hydroxide or potassium hydroxide.

4. The process of claim 1 comprising feeding the alkali hydroxide in a plurality of portions during the course of the hydrolysis.

5. The process of claim 1 including the additional step of driving off the water from the hydrolysis mixture at a temperature above 130° C.

6. The process of claim 1 wherein the hydrolysis is carried out at 135° to 200° C. using 0.3 to 3.0 moles of alkali hydroxide per 100 mole of nicotinonitrile, the alkali hydroxide is sodium hydroxide or potassium hydroxide and the water is driven off at a temperature of 140° to 200° C.

7. The process of claim 1 wherein the materials employed consist of nicotinonitrile, water, and alkali metal hydroxide.

8. The process of claim 7 wherein the alkali metal hydroxide is sodium hydroxide.

9. The process of claim 2 wherein the alkali metal hydroxide is sodium hydroxide.

10. The process of claim 1 wherein the hydrolysis is carried out during a time of 1 to 20 minutes.

11. The process of claim 10 wherein the hydrolysis is carried out in a time of 3 to 15 minutes.

12. The process of claim 10 wherein the alkali hydroxide is sodium hydroxide or potassium hydroxide and there are used 0.3 to 3.0 moles of alkali hydroxide per 100 moles of nicotinonitrile.

* * * * *